United States Patent
Simon et al.

(10) Patent No.: US 7,459,462 B2
(45) Date of Patent: Dec. 2, 2008

(54) FREDERICAMYCIN DERIVATIVES

(75) Inventors: Werner Simon, Hüffelsheim (DE); Ulrich Abel, Heidelberg (DE)

(73) Assignee: Biofrontera Discovery GmbH (DE)

( * ) Notice: Subject to any disclaimer, the term of this patent is extended or adjusted under 35 U.S.C. 154(b) by 340 days.

(21) Appl. No.: 10/511,411

(22) PCT Filed: Mar. 28, 2003

(86) PCT No.: PCT/EP03/03285

§ 371 (c)(1), (2), (4) Date: Oct. 14, 2004

(87) PCT Pub. No.: WO03/087060

PCT Pub. Date: Oct. 23, 2003

(65) Prior Publication Data

US 2005/0153997 A1 Jul. 14, 2005

(30) Foreign Application Priority Data

Apr. 17, 2002 (DE) .................. 102 17 046

(51) Int. Cl.
*A61K 31/473* (2006.01)
*C07D 221/20* (2006.01)

(52) U.S. Cl. .............. 514/278; 546/15; 546/18
(58) Field of Classification Search ............... 514/278; 546/15, 18
See application file for complete search history.

(56) References Cited

U.S. PATENT DOCUMENTS

| 4,584,377 A | 4/1986 | Yokoi et al. |
| 4,673,678 A | 6/1987 | Misra |
| 5,166,208 A | 11/1992 | Kelly et al. |

OTHER PUBLICATIONS

Latham, M.D., et al., "Inhibition of topoisomerases by fredericamycin A", Cancer Chemotherapy and Pharmacology 24:167-171 (1989).

*Primary Examiner*—Charanjit S. Aulakh
(74) *Attorney, Agent, or Firm*—Connolly Bove Lodge & Hutz LLP

(57) ABSTRACT

The invention relates to novel fredericamycin derivatives, to medicaments containing these derivatives or salts thereof, and to the use of fredericamycin derivatives for treating diseases, particularly tumor diseases.

7 Claims, No Drawings

FREDERICAMYCIN DERIVATIVES

The invention relates to novel fredericamycin derivatives, to drugs containing said derivatives or the salts thereof, and to the use of the fredericamycin derivatives for treating diseases, particularly tumor diseases.

Fredericamycin has been isolated 1981 from *Streptomyces griseus*, and demonstrates anti-tumor activity.

Fredericamycin and several fredericamycin derivatives are known.

In Heterocycles 37 (1994) 1893-1912, J. Am. Chem. Soc. 116 (1994) 9921-9926, J. Am. Chem. Soc. 116 (1994) 11275-11286, J. Am. Chem. Soc. 117 (1995) 11839-11849, JP 2000-072752, and in J. Am. Chem. Soc. 123 (2001), various total syntheses of fredericamycin A have been described, some being enantio-selective.

In U.S. Pat. No. 4,673,768, alkali salts of the fredericamycin A are described. In U.S. Pat. No. 4,584,377, fredericamycin derivatives are described, particularly derivatives acylated in ring E and F. In U.S. Pat. No. 5,166,208, fredericamycin derivatives are described as well, particularly derivatives carrying thio and amino substituents in ring F. The derivatives are generated semi-synthetically or fully synthetically.

Surprisingly it was found that fredericamycin derivatives, especially those derivatized in ring A, represent potent drugs. Also, a possibility was found to introduce such residues in ring A semi-synthetically, with which the water solubility, among others, can be significantly increased. Other derivatisation methods known from the art can also be performed with the derivatives according to the invention. Furthermore, an alternative method was found to make fredericamycin derivatives water-soluble by generating cyclodextrin inclusion compounds.

The invention relates to novel fredericamycin derivatives with the general Formula Ia or Ib:

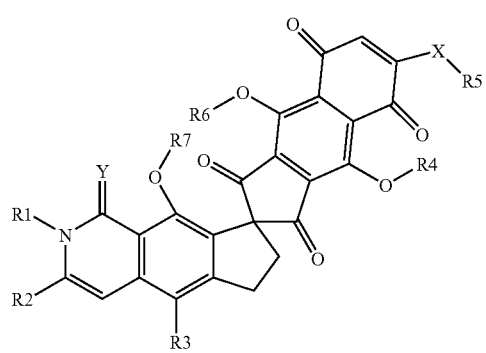

Ia

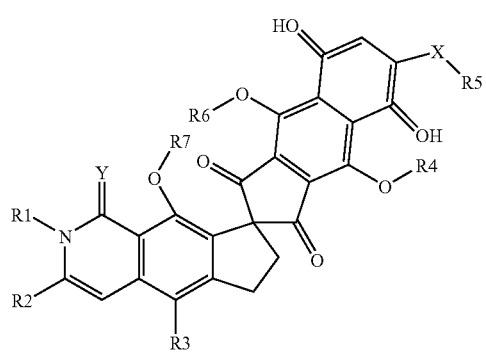

Ib wherein in each,

R1 means H, $C_1$-$C_6$ alkyl, cycloalkyl, $C_1$-$C_4$ alkylcycloalkyl,

R2 means $C_1$-$C_{14}$ alkyl, $C_2$-$C_{14}$ alkenyl, 1,3-butadienyl, 1-butane, $C_1$-$C_4$ alkylaryl, heteroaryl, $C_1$-$C_4$ alkyl heteroaryl, cycloalkyl, $C_1$-$C_4$ alkyl-cycloalkyl, heterocycloalkyl, $C_1$-$C_4$ alkylheterocycloalkyl, $C_mH_{2m+o-p}Y''_p$ (with m=1 to 6, for o=1, p=1 to 2m+o; for m=2 to 6, o=−1, p=1 to 2m+o; for m=4 to 6, o=−2, p=1 to 2m+o; Y''=independently from each other selected from the group consisting of halogen, OH, OR21, $NH_2$, NHR21, NR21R22, SH, SR21), $CH_2NHCOR21$, $CH_2NHCSR21$, $CH_2S(O)nR21$, with n=0, 1, 2, $CH_2SCOR21$, $CH_2OSO_2$—R21, CHO, CH=NOH, CH(OH)R21, —CH=NOR21, —CH=NOCOR21, —CH=NOCH$_2$CONR21R22, —CH=NOCH($CH_3$)CONR21R22, —CH=NOC($CH_3$)$_2$CONR21R22, —CH=N—NHCO—R23, —CH=N—NHCO—CH$_2$NHCOR21, —CH=N—O—CH$_2$NHCOR21, —CH=N—NHCS—R23, —CH=CR24R25 (trans or cis), COOH, COOR21, CONR21R22, —CH=NR21, —CH=N—NR21R22,

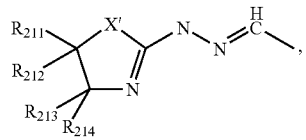

with X'=NR215, O, S, and R211, R212, R213, R214, R215 being independently from each other H or $C_1$-$C_6$ alkyl), —CH=N—NHSO$_2$ aryl, —CH=N—NHSO$_2$-heteroaryl, R21, R22 are independently from each other $C_1$-$C_{14}$ alkyl, $C_1$-$C_{14}$ alkanoyl, $C_1$-$C_6$ alkylhydroxy, $C_1$-$C_6$ alkylamino, $C_1$-$C_6$ alkylamino-$C_1$-$C_6$ alkyl, $C_1$-$C_6$ alkylamino-di-$C_1$-$C_6$ alkyl, cycloalkyl, $C_1$-$C_4$ alkylcycloalkyl, heterocycloalkyl, $C_1$-$C_4$ alkylheterocycloalkyl, aryl, aryloyl, $C_1$-$C_4$ alkylaryl, heteroaryl, heteroaryloyl, $C_1$-$C_4$ alkylheteroaryl, cycloalkanoyl, $C_1$-$C_4$ alkanoylcycloalkyl, heterocycloalkanoyl, $C_1$-$C_4$ alkanoylheterocycloalkyl, $C_1$-$C_4$ alkanoylaryl, $C_1$-$C_4$ alkanoylheteroaryl, mono- and di-sugar residues linked through a C atom which would carry an OH residue in the sugar, wherein the sugars are independently from each other selected from the group consisting of glucuronic acid and its stereo isomers at all optical atoms, aldopentoses, aldohexoses, including their desoxy compounds (such as e.g. glucose, desoxyglucose, ribose, desoxyribose), R23 independently of R21, has the same meanings as R21, or $CH_2$-pyridinium salts, $CH_2$-tri-$C_1$-$C_6$ alkylammonium salts, R24 independently of R21, has the same meanings as R21, or H, CN, $COCH_3$, COOH, COOR21, CONR21R22, $NH_2$, NHCOR21, R25 independently of R21, has the same meanings as R21, or H, CN, $COCH_3$, COOH, COOR21, CONR21 R22, $NH_2$, NHCOR21, R24, R25 together mean $C_4$-$C_8$ cycloalkyl, R3 means $C_2$-$C_{14}$ alkyl, $C_2$-$C_{14}$ alkenyl, $C_2$-$C_{14}$ alkinyl, aryl, $C_1$-$C_4$ alkylaryl, heteroaryl, $C_1$-$C_4$ alkylheteroaryl, wherein the aryls or heteroaryls may be substituted with another aryl, $C_1$-$C_4$ alkylaryl, O-aryl, $C_1$-$C_4$ alkyl-O-aryl, heteroaryl, $C_1$-$C_4$ alkylheteroaryl, O-heteroaryl or $C_1$-$C_4$ alkyl-O-heteroaryl, cycloalkyl, $C_1$-$C_4$ alkylcycloalkyl, heterocycloalkyl, $C_1$-$C_4$ alkylheterocycloalkyl, $C_mH_{2m+o-p}Y'_p$ (with m=2 to 6, for o=1, −1, p=1 to 2m+o; for m=4 to 6, o=−3, p=1 to 2m+o; Y'=independently from each other selected from the group consisting of halogen, OH, OR31, NH₂, NHR31, NR31R32, SH, SR31), CH₂NHCOR31, CH₂NHCSR31, CH₂S(O)nR31, with n=0, 1, 2, CH₂SCOR31, CH₂OSO₂—R31, CHO, CH=NOH, CH(OH)R31, —CH=NOR31, —CH=NOCOR31, —CH=NOCH₂CONR31R32, —CH=NOCH(CH₃)CONR31R32, —CH=NOC(CH₃)₂CONR31R32, —CH=N—NHCO—R33, —CH=N—NHCO—CH₂NHCOR31, —CH=N—O—CH₂NHCOR31, —CH=N—NHCS—R33, —CH=CR34R35 (trans or cis), COOH, COOR31, CONR31R32, —CH=NR31, —CH=N—NR31R32,

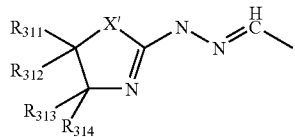

(with X'=NR315, O, S, and R311, R312, R313, R314, R315 being independently from each other H or $C_1$-$C_6$ alkyl), —CH=N—NHSO₂-aryl, —CH=N—NHSO₂-heteroaryl, R31, R32 mean independently from each other $C_1$-$C_{14}$ alkyl, $C_1$-$C_{14}$ alkanoyl, $C_1$-$C_6$ alkylhydroxy, $C_1$-$C_6$ alkylamino, $C_1$-$C_6$alkylamino-$C_1$-$C_6$ alkyl, $C_1$-$C_6$ alkylamino-di-$C_1$-$C_6$ alkyl, cycloalkyl, $C_1$-$C_4$ alkylcycloalkyl, heterocycloalkyl, $C_1$-$C_4$ alkylheterocycloalkyl, aryl, aryloyl, $C_1$-$C_4$ alkylaryl, heteroaryl, heteroaryloyl, $C_1$-$C_4$ alkylheteroaryl, cycloalkanoyl, $C_1$-$C_4$ alkanoylcycloalkyl, heterocycloalkanoyl, $C_1$-$C_4$ alkanoylheterocycloalkyl, $C_1$-$C_4$ alkanoylaryl, $C_1$-$C_4$ alkanoylheteroaryl, mono- and di-sugar residues linked through a C atom which would carry an OH residue in the sugar, wherein the sugars are independently from each other selected from the group consisting of glucuronic acid and its stereo isomers at all optical atoms, aldopentoses, aldohexoses, including their desoxy compounds (such as e.g. glucose, desoxyglucose, ribose, desoxyribose), R33 independently of R31, has the same meanings as R31, or CH₂-pyridinium salts, CH₂-tri-$C_1$-$C_6$ alkylammonium salts, R34 independently of R21, has the same meanings as R31, or H, CN, COCH₃, COOH, COOR21, CONR31R32, NH₂, NHCOR31, R35 independently of R31, has the same meanings as R31, or H, CN, COCH₃, COOH, COOR31, CONR31R32, NH₂, NHCOR31, R34, R35 together mean $C_4$-$C_8$ cycloalkyl, R5 means H, $C_1$-$C_6$ alkyl, cycloalkyl, $C_1$-$C_4$ alkylcycloalkyl, heterocycloalkyl, $C_1$-$C_4$ alkylheterocycloalkyl, aryl, $C_1$-$C_4$ alkylaryl, heteroaryl, $C_1$-$C_4$ alkylheteroaryl, R4, R6, R7 independently from each other mean H, $C_1$-$C_6$ alkyl, CO—R41, R41 independently of R21, has the same meanings as R21, X means O, S, NH, N—R8, wherein R8 independently from R5 may adopt the same meaning as R5, or R5 and R8, together with the N, form a ring with 4, 5, 6, 7, or 8 members, which may optionally contain still another heteroatom selected from the group N, O, S, or X-R5 may together be H, Y means O, S, NR9, wherein R9 may be H or $C_1$-$C_6$ alkyl, as well their stereoisomers, tautomers, and their physiologically tolerable salts or inclusion compounds.

Preferred are compounds of Formula IIa or IIb

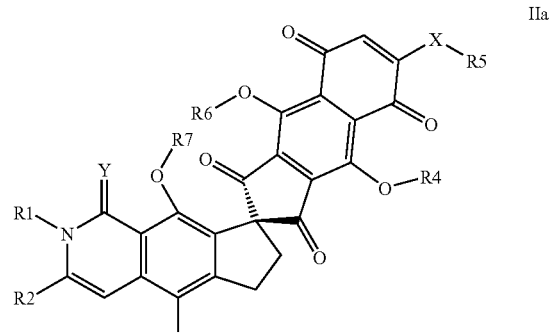

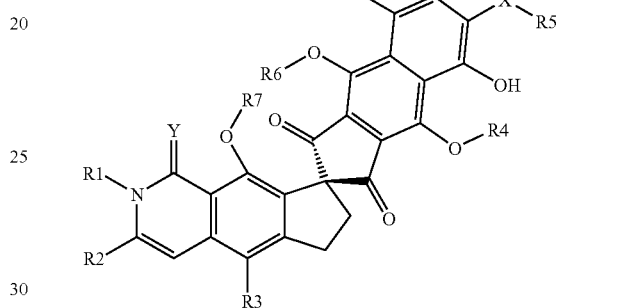

wherein the meaning of the residues R1-R41, X is as described above, their tautomers and their physiologically tolerable salts or inclusion compounds.

The invention further relates to compounds of Formulas Ia, Ib, IIa or IIb, in which the residues R, except for R3, have the above described meanings, and the water solubility of R3 is at least two times higher, preferably at least five timer higher, more preferred at least ten times higher, especially preferred at least fifty time higher, particularly one hundred times higher, or even five hundred times higher than of R3 being H, when all other residues are maintained. The increase in the water solubility is achieved e.g. by introduction of groups which can increasingly form hydrogen bonds, and/or are polar, and/or are ionic. Residues R3 with increased water solubility und with the meaning indicated in the formulas are preferred.

The invention also relates to compounds of the Formula Ia, Ib, IIa or IIb, in which the residues R, except R2, have the above described meanings, and, additionally, the water solubility of R2 is at least two times higher, preferably at least five timer higher, more preferred at least ten times higher, especially preferred at least fifty time higher, particularly one hundred times higher, or even five hundred times higher than of R2 being CH=CH—CH=CH—CH₃, when all other residues are maintained. The increase in water solubility is mediated e.g. by introduction of groups which can increasingly form hydrogen bonds and/or are polar and/or are ionic. A key intermediate are compounds with an aldehyde function in R2. Residues R2 with increased water solubility and with the meaning indicated in the Formulas are preferred. Especially preferred are derivatives with increased water solubility in R2 and R3.

Preferred R2 residues are heteroaryl, cycloalkyl, $C_1$-$C_4$ alkylcycloalkyl, heterocycloalkyl, $C_1$-$C_4$ alkylheterocycloalkyl, $C_mH_{2m+o-p}Y''_p$ (with m=1 to 6, for o=1, p=1 to 2m+o; for m=2 to 6, o=−1, p=1 to 2m+o; for m=4 to 6, o=−2, p=1 to 2m+o; Y''=independently selected from each other from the group of halogen, OH, OR21, $NH_2$, NHR21, NR21R22, SH, SR21), $CH_2$NHCOR21, $CH_2$NHCSR21, $CH_2$S(O)nR21, with n=0, 1, 2, $CH_2$SCOR21, $CH_2$OSO$_2$—R21, CH(OH)R21, —CH=NOCOR21, —CH=NOCH$_2$CONR21R22, —CH=NOCH(CH$_3$)CONR21R22, —CH=NOC(CH$_3$)$_2$CONR21R22, —CH=N—NHCO—R23, —CH=N—NHCO—CH$_2$NHCOR21, —CH=N—O—CH$_2$NHCOR21, —CH=N—NHCS—R23, —CH=CR24R25 (trans or cis), CONR21R22, —CH=NR21, —CH=N—NR21R22,

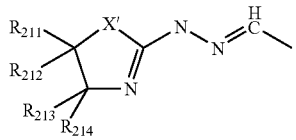

(with X'=NR215, O, S, and R211, R212, R213, R214, R215 being independently from each other H or $C_1$-$C_6$ alkyl), —CH=N—NHSO$_2$ aryl, —CH=N—NHSO$_2$ heteroaryl.

Furthermore preferred are still compounds as described above, wherein the residues R preferably independently from each other adopt one or more of the following meanings:

R1 means H, $C_1$-$C_5$ alkyl, cycloalkyl, especially H,

R2 means $C_1$-$C_5$ alkyl, $C_1$-$C_4$ alkylaryl, $C_2$-$C_5$alkenyl, heteroaryl, $C_1$-$C_4$ alkylheteroaryl, CHF$_2$, CF$_3$, polyol side chain, particularly CHOH—CHOH—CHOH—CHOH—CH$_3$, CHOH—CHOH—CH=CH—CH$_3$, CH=CH—CHOH—CHOH—CH$_3$, CH$_2$Y'''(Y'''=F, Cl, Br, I), CH$_2$NH$_2$, CH$_2$NR21R22, CH$_2$NHCOR23, CH$_2$NHCSR23, CH$_2$SH, CH$_2$S(O)nR21, with n=0, 1, 2, CH$_2$SCOR21, particularly CH$_2$OH, CH$_2$OR21, CH$_2$OSO$_2$—R21, particularly CHO, CH(OR21)$_2$, CH(SR21)$_2$, CN, CH=NOH, CH=NOR21, CH=NOCOR21, CH=N—NHCO—R23, CH=CR24, R25 (trans or cis), particularly COOH (particularly their physiologically tolerable salts), COOR21, CONR21R22, —CH=NR21, —CH=N—NR21R22,

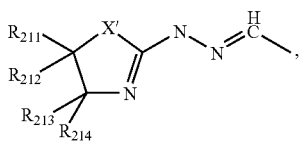

(with X'=NR215, O, S, and R211, R212, R213, R214, R215 being independently from each other H or $C_1$-$C_6$ alkyl), —CH=N—NHSO$_2$ aryl, —CH=N—NHSO$_2$ heteroaryl, CH=N—NHCO—R23, R21, R22 independently from each other mean $C_1$-$C_6$ alkyl, cycloalkyl, aryl, $C_1$-$C_4$ alkylaryl, heteroaryl, $C_1$-$C_4$ alkylheteroaryl, R23 independently of R21, has the same meanings as R21, or CH$_2$-pyridinium salts, CH$_2$-tri-$C_1$-$C_6$ alkylammonium salts, R24 independently of R21, has the same meanings as R21, or H, CN, COCH$_3$, COOH, COOR21, CONR21R22, NH$_2$, NHCOR21, R25 independently of R21, has the same meanings as R21, or H, CN, COCH$_3$, COOH, COOR21, CONR21R22, NH$_2$, NHCOR21, R24, R25 together mean $C_4$-$C_8$ cycloalkyl, R3 means $C_2$-$C_{14}$ alkyl, $C_2$-$C_{14}$ alkenyl, $C_2$-$C_{14}$ alkinyl, aryl, $C_1$-$C_4$ alkylaryl, heteroaryl, $C_1$-$C_4$ alkylheteroaryl, wherein the aryls or heteroaryls may be substituted with another aryl, $C_1$-$C_4$ alkylaryl, O-aryl, $C_1$-$C_4$ alkyl-O-aryl, heteroaryl, $C_1$-$C_4$ alkylheteroaryl, O-heteroaryl or $C_1$-$C_4$ alkyl-O-heteroaryl, R5 means H, $C_1$-$C_3$ alkyl, cycloalkyl, R4, R6, R7 independently from each other mean H, $C_1$-$C_5$ alkyl, CO—R41, R41 independently of R21, has the same meanings as R21, X means O, S, NH, N—R8, particularly O, Y means O, S, NH, particularly O, their stereoisomers, tautomers, and their physiologically tolerable salts or inclusion compounds.

Most preferred are the compounds, the stereo isomers, tautomers, and physiologically tolerable salts or inclusion compounds of which, selected from the group consisting of the compounds of the examples 7-10, and the compounds demonstrating combinations of the various substituents of the compounds of these examples.

Also preferred are drugs which contain the above compounds of Formula I or II in addition to the usual carriers and adjuvants.

Also preferred are the above mentioned drugs in combination with other agents for tumor treatment.

These compounds according to the invention are used for preparation of drugs for treatment of tumors, particularly such that may be treated by inhibition of the topoisomerases I and/or II. Tumors that can be treated with the substances according to the invention are e.g. leukemia, lung cancer, melanomas, prostate tumors and colon tumors.

Furthermore, the compounds according to the invention can be used for preparation of drugs for treatment of neurodermitis, parasites and for immunosuppression.

In the description and the claims the substituents are described by the following definitions:

The term "alkyl" by itself or as part of another substituent means a linear or branched alkyl chain radical of the respectively indicated length, in which optionally a CH$_2$ group may be substituted by a carbonyl function. Thus, $C_{1-4}$ alkyl may be methyl, ethyl, 1-propyl, 2-propyl, 2-methyl-2-propyl, 2-methyl-1-propyl, 1-butyl, 2-butyl, $C_{1-6}$ alkyl, e.g. $C_{1-4}$ alkyl, pentyl, 1-pentyl, 2-pentyl, 3-pentyl, 1-hexyl, 2-hexyl, 3-hexyl, 4-methyl-1-pentyl, or 3,3-dimethylbutyl.

The term "$C_1$-$C_6$ alkylhydroxy" by itself or as part of another substituent means a linear or branched alkyl chain radical of the respectively indicated length, which may be saturated or unsaturated, and which carries an OH group, e.g. hydroxymethyl, hydroxymethyl, 1-hydroxypropyl, 2-hydroxypropyl.

The term "alkenyl" by itself or as part of another substituent means a linear or branched alkyl chain radical with one or more C=C double bonds of the respectively indicated length, several double bonds being preferably conjugated. Thus, $C_{2-6}$ alkenyl may for example be ethenyl, 1-propenyl, 2-propenyl, 2-methyl-2-propenyl, 2-methyl-1-propenyl, 1-butenyl, 2-butenyl, 1,3-butdienyl, 2,4-butdienyl, 1-pentenyl, 2-pentenyl, 3-pentenyl, 1,3-pentdienyl, 2,4-pentdienyl, 1,4-pentdienyl, 1-hexenyl, 2-hexenyl, 1,3-hediexyl, 4-methyl-1-pentenyl, or 3,3-dimethylbutenyl.

The term "alkinyl" by itself or as part of another substituent means a linear or branched alkyl chain radical with one or more C—C triple bonds of the respectively indicated length, wherein additional double bonds may be present as well. Thus, $C_{2-6}$ alkinyl may for example be ethinyl, 1-propinyl, 2-propinyl, 2-methyl-2-propinyl, 2-methyl-1-propinyl, 1-butinyl, 2-butinyl, 1-pentinyl, 2-pentinyl, 3-pentinyl, 1,4-pentdiinyl, 1-pentine-4-enyl, 1-hexinyl, 2-hexinyl, 1,3-hexdiinyl, 4-methyl-1-pentinyl, or 3,3-dimethylbutinyl.

The term "halogen" stands for fluorine, chlorine, bromine, iodine, preferably bromine and chlorine.

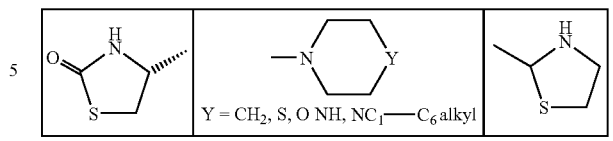

The term "aryl" by itself or as part of another substituent includes aromatic ring systems with up to 3 rings, in which at least 1 ring system is aromatic, and those with up to 3 substituents, preferably up to 1 substituent, wherein the substituents independently from each other can have the meaning $C_1$-$C_6$ alkyl, OH, $NO_2$, CN, $CF_3$, OR11, SH, SR11, $C_1$-$C_6$ alkylhydroxy, $C_1$-$C_6$ alkyl-OR11, COOH, COOR11, CONH2, CONR11R12, CHO, CH=NO—$C_1$-$C_{10}$ alkyl, $C_1$-$C_{10}$ alk-1-enyl, $NH_2$, NHR11, NR11R12, halogen, wherein the residues R11 und R12 independently from each other can mean $C_1$-$C_{10}$ alkyl, cycloalkyl, $C_1$-$C_4$ alkylcycloalkyl.

Apart from phenyl and 1-naphthyl and 2-naphthyl, preferred aryls are:

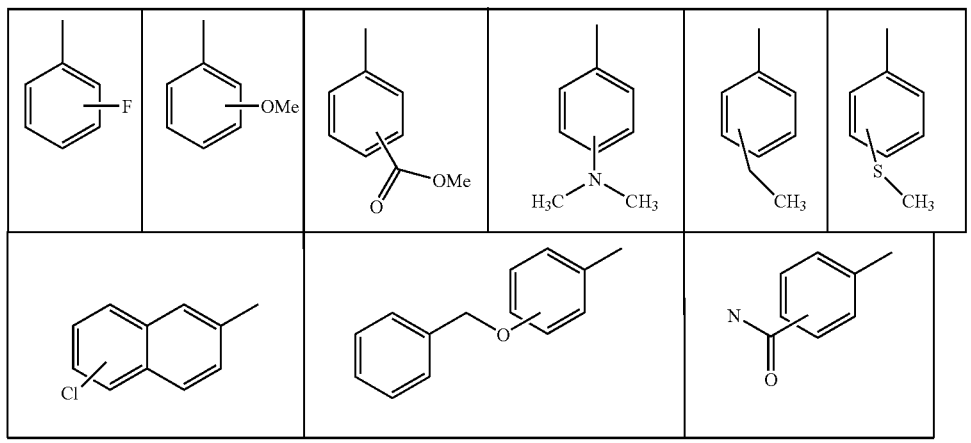

The term "NR21R22", or analogous NRx1Rx2, preferably stand for a dialkylamino group, wherein the two alkyl groups together with the N can form a ring with 5 or 6 members with optionally one more heteroatom N or O.

The term "cycloalkyl" by itself or as part of another Substituent comprises saturated, cyclic carbohydrate groups with 3 to 8 C atoms, such as e.g. cyclopropyl, cyclobutyl, cyclopentyl, cyclohexyl, 4-methylcyclohexyl, cyclohexylmethylene, cycloheptyl or cyclooctyl.

The term "heterocycloalkyl" by itself or as part of another substituent includes cycloalkyl groups, wherein up to two $CH_2$ groups may be substituted by oxygen, sulfur or nitrogen atoms, and another $CH_2$ group may be substituted by a carbonyl function, for example pyrrolidine, piperidine, morpholine or The term "heteroaryl" by itself or as part of another substituent includes aromatic ring systems with up to 3 rings and with up to 3 identical or different heteroatoms N, S, O, in which at least 1 ring system is aromatic, and those with up to 3 substituents, preferably up to 1 substituent, wherein the substituents independently from each other can have the meaning $C_1$-$C_6$ alkyl, OH, $NO_2$, CN, $CF_3$, OR11, SH, SR11, $C_1$-$C_6$ alkylhydroxy, $C_1$-$C_6$ alkyl-OR11, COOH, COOR11, $CONH_2$, CONR11R12, CHO, CH=NO—$C_1$-$C_{10}$ alkyl, $C_1$-$C_{10}$ alk-1-enyl, $NH_2$, NHR11, NR11R12, halogen, wherein the residues R11 und R12 independently from each other can mean $C_1$-$C_{10}$ alkyl, cycloalkyl, $C_1$-$C_4$ alkylcycloalkyl.

Preferred heteroaryls are:

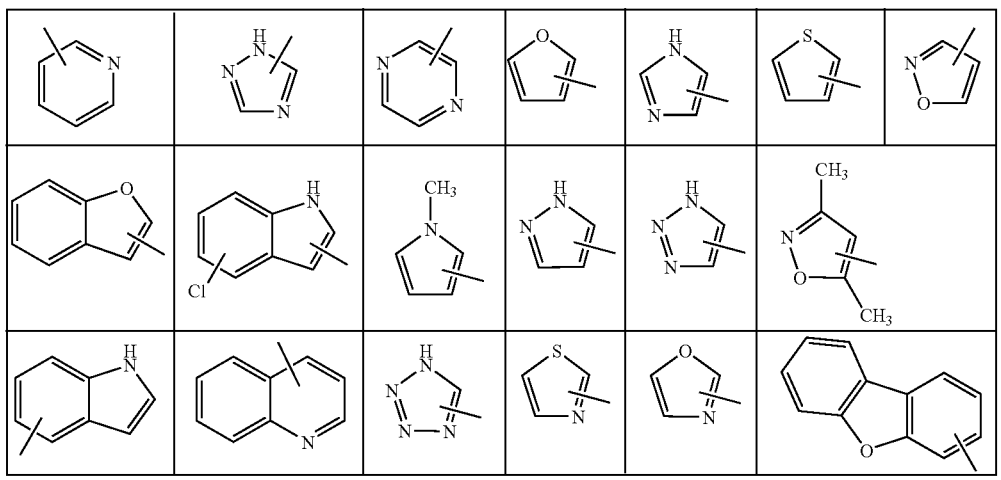

Particularly preferred are 2-furyl, 3-furyl, 2-thiophenyl, 3-thiophenyl, 3-pyridinyl, 4-pyridinyl, 4-isoxazolyl, 2-N-methylpyrrolyl, and 2-pyrazinyl. Especially preferred are these as residues R3.

The term "ring system" generally refers to rings with 3, 4, 5, 6, 7, 8, 9, or 10 members. Preferred are rings with 5 and 6 members. Furthermore, ring systems with one or 2 annelated rings are preferred.

The compounds of Formula I may be present as such, or, if they contain acidic or basic groups, in the form of their salts with physiologically tolerable bases or acids. Examples for such acids are: hydrochloric acid, citric acid, trifluoracetic acid, tartaric acid, lactic acid, phosphoric acid, methane sulfonic acid, acetic acid, formic acid, maleic acid, fumaric acid, succinic acid, hydroxysuccinic acid, sulfuric acid, glutaric acid, aspartic acid, pyruvic acid, benzoic acid, glucuronic acid, oxalic acid, ascorbic acid, and acetylglycine. Examples for bases are alkali ions, preferably Na, K, alkaline earth ions, preferably Ca, Mg, ammonium ions.

The compounds according to the invention may be administered orally in the usual way. The application may also be i.v., i.m., with vapors, or sprays through the nasopharynx.

The dosage depends on age, condition and weight of the patient as well as on the type of application. Usually, the daily dose of the active ingredient per person is between 0.1 µg/kg and 1 g/kg orally. This dosage may be given as 2 to 4 split dosages, or once per day as a slow release form.

The novel compounds may be used in the usual solid or liquid pharmaceutical application forms, e.g. as tablets, film tablets, capsules, powder, granules, coated tablets, solutions, or sprays. These are prepared in the usual way. The agents can be processed with the usual pharmaceutical adjuvants such as tablet binders, fillers, preservatives, disintegrants, flow regulators, plasticizers, wetting agents, dispersants, emulsifiers, solvents, retardation agents, antioxidants, and/or propellants (see H. Sucker et al.: Pharmazeutische Technologie, Thieme-Verlag, Stuttgart, 1978). Usually, the so obtained application forms contain the active ingredient in amounts of 0.1 to 99 percent per weight.

Experimental Part

Fredericamycin A can be prepared by fermentation or fully synthetically according to the known methods. The reduced forms of the Formulas Ib and IIb can be obtained from the appropriate compounds of Formulas Ia and IIa using mild reducing agents.

PREPARATION OF THE SUBSTANCES

Substitution at the B ring

Palladium-catalyzed C—C bond

Fredericamycin (1) can be reacted with halogenization agents such as N-bromosuccinimide (NBS) and N-iodosuccinimide (NIS) to the 5-bromo- or 5 iodofredericamyin derivatives (2) and (3) with good yields (diagram 1).

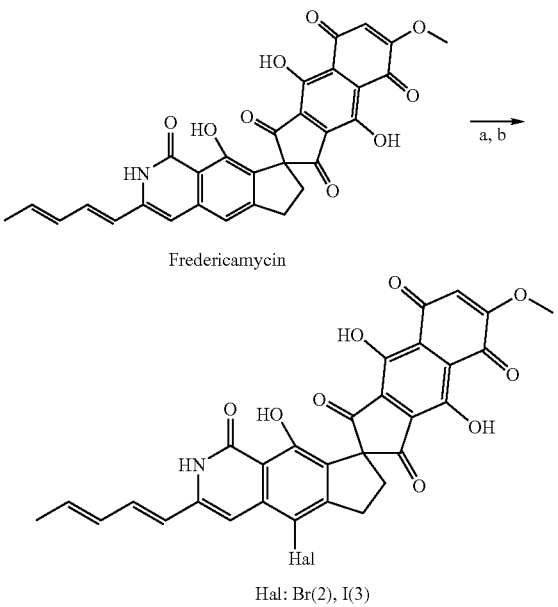

Diagram 1

Fredericamycin

Hal: Br(2), I(3)
a) N-bromosuccinimide, DMF, 0° C.;
b) N-iodosuccinimide, DMF, 0° C.

By palladium-catalyzed cross couplings according to Suzuki, Stille or according to Heck, with organoboron compounds or stannous compounds such as, e.g. trans-1-hexene- 1yl-boronic acid (4), phenylboronic acid (5), and 4-fluorophenylboronic acid (6), the appropriate C—C-linked fredericamycin derivatives (7), (8) and (9) are accessible (see diagram 2).

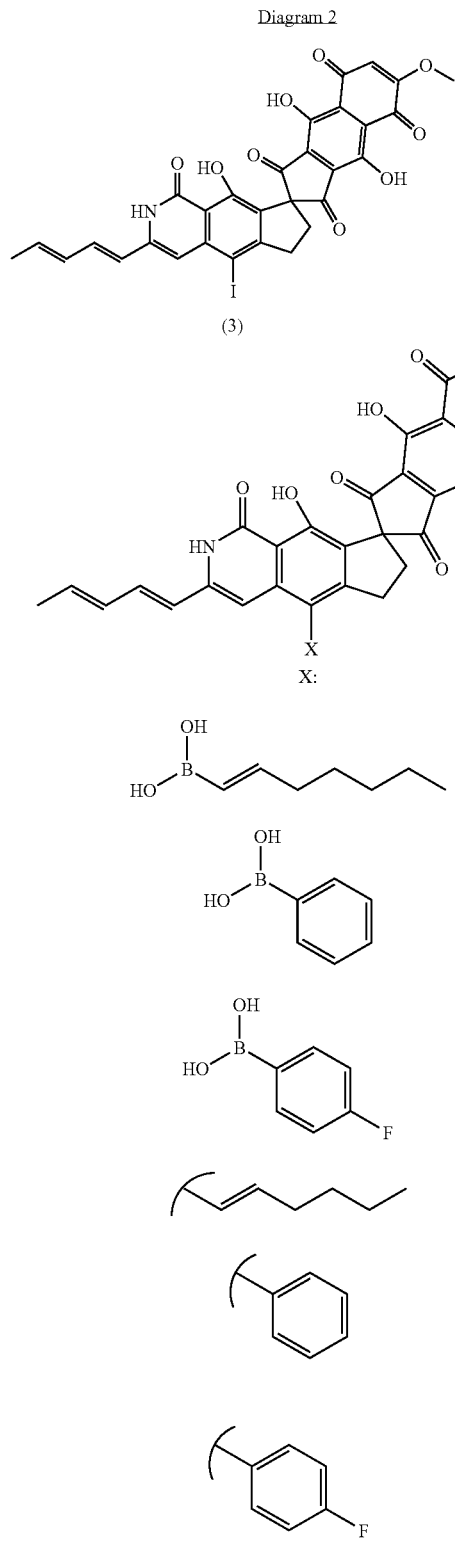

a) trans-1-hexene-1 yl-boronic acid (4), Pd(PPh₃)₄, Na₂CO₃
b) phenylboronic acid, Pd(PPh₃)₄, (5), Na₂CO₃
c) 4-fluorophenylboronic acid Also, derivatives with X equaling an aldehyde function can be prepared according to diagrams 3 and 4. For example for the sequence X equaling 1) Br, 2) pentadienyl, 3) tetrol, 4) aldehyde. The other derivatizations according to the inventions are then possible through the aldehyde function.

For the synthesis of further water soluble fredericamycin derivatives, fredericamycin (1) was first hydroxylated with osmium(IV)oxide at the diene side chain.

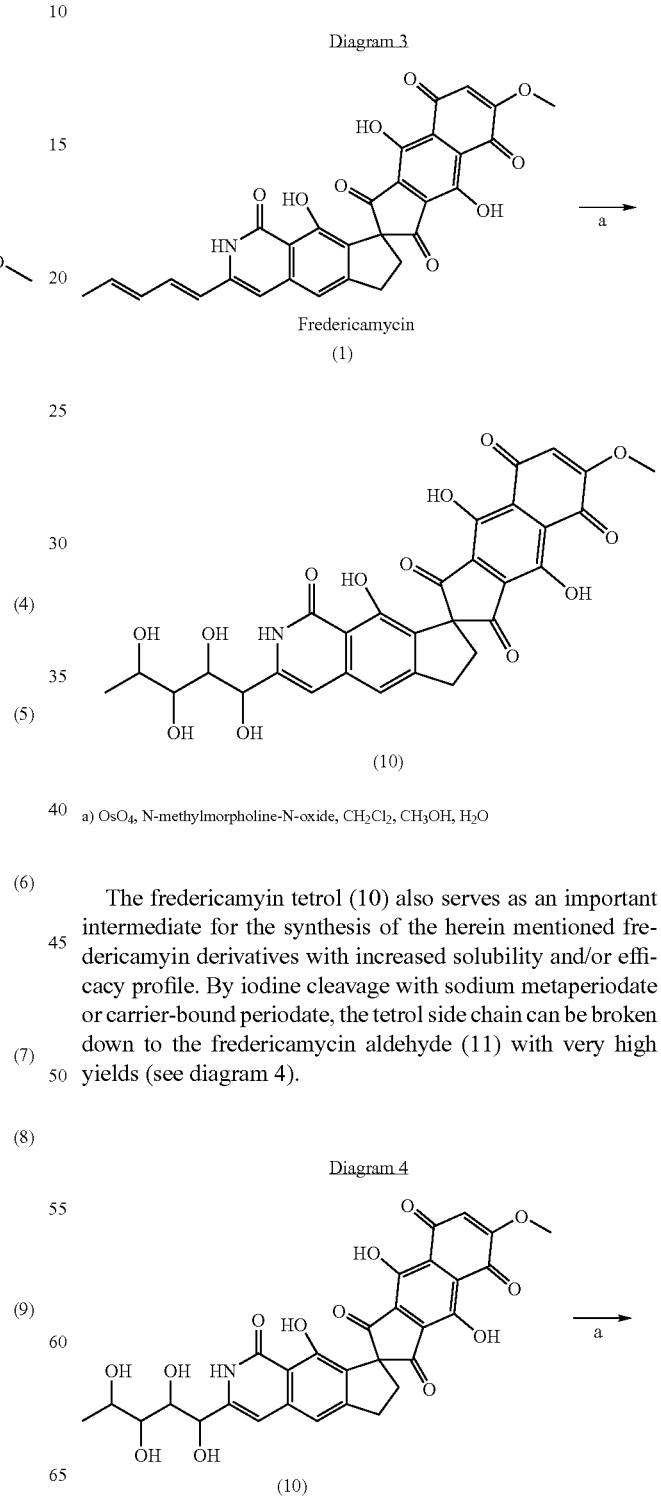

a) OsO₄, N-methylmorpholine-N-oxide, CH₂Cl₂, CH₃OH, H₂O

The fredericamyin tetrol (10) also serves as an important intermediate for the synthesis of the herein mentioned fredericamyin derivatives with increased solubility and/or efficacy profile. By iodine cleavage with sodium metaperiodate or carrier-bound periodate, the tetrol side chain can be broken down to the fredericamycin aldehyde (11) with very high yields (see diagram 4).

-continued

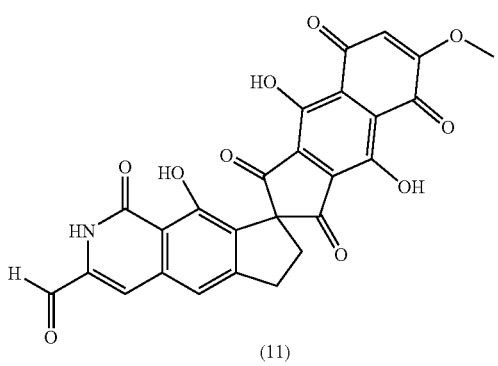

(11)

a) NaIO₄—H₂O—DMF or carrier-bound ——IO₄—H₂O—DMF

This aldehyde may be reacted by bromating reagents such as N-bromosuccinimide, bromine or other bromine generating reagents to a compound that is bromated in the nucleus (12) (see diagram 5).

Diagram 5

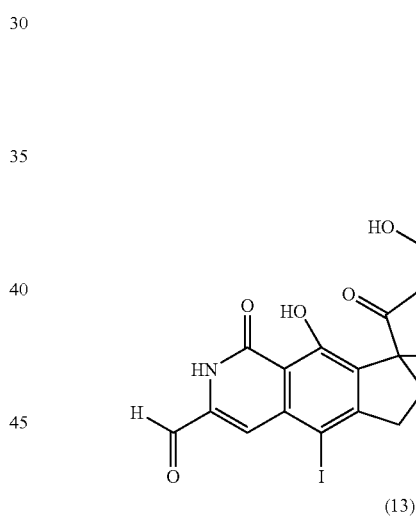

(11)
Fredericamycin (12)

Surprisingly it also was shown, that fredericamycin aldehyde iodated in the nucleus (13) is generated in one step of the above described diol cleavage [(10)→(11)]. This surprising reaction is only observed, if dimethylsulfoxide (DMSO) is used as a solvent instead of dimethylformamide (DMF) (see diagram 6).

Diagram 6

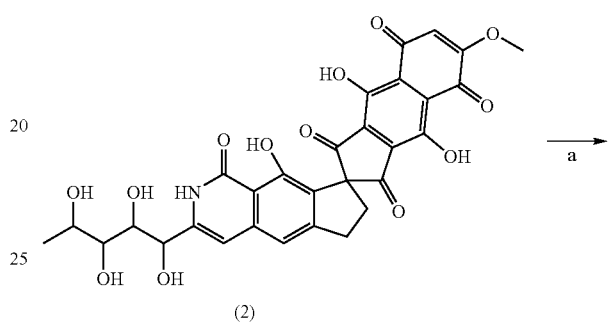

(2)

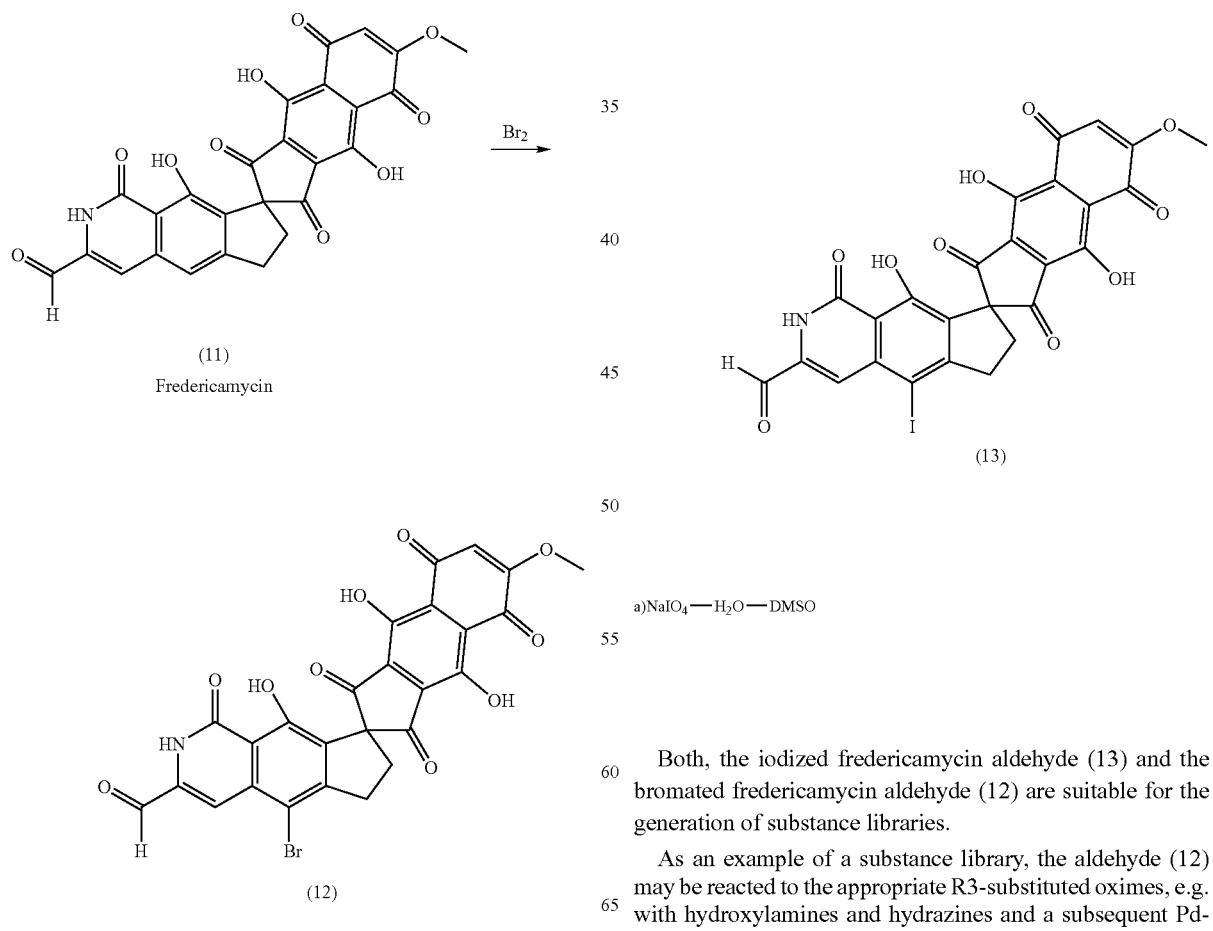

(13)

a)NaIO₄—H₂O—DMSO

Both, the iodized fredericamycin aldehyde (13) and the bromated fredericamycin aldehyde (12) are suitable for the generation of substance libraries.

As an example of a substance library, the aldehyde (12) may be reacted to the appropriate R3-substituted oximes, e.g. with hydroxylamines and hydrazines and a subsequent Pd-catalyzed C—C coupling (see diagram 7).

Diagram 7

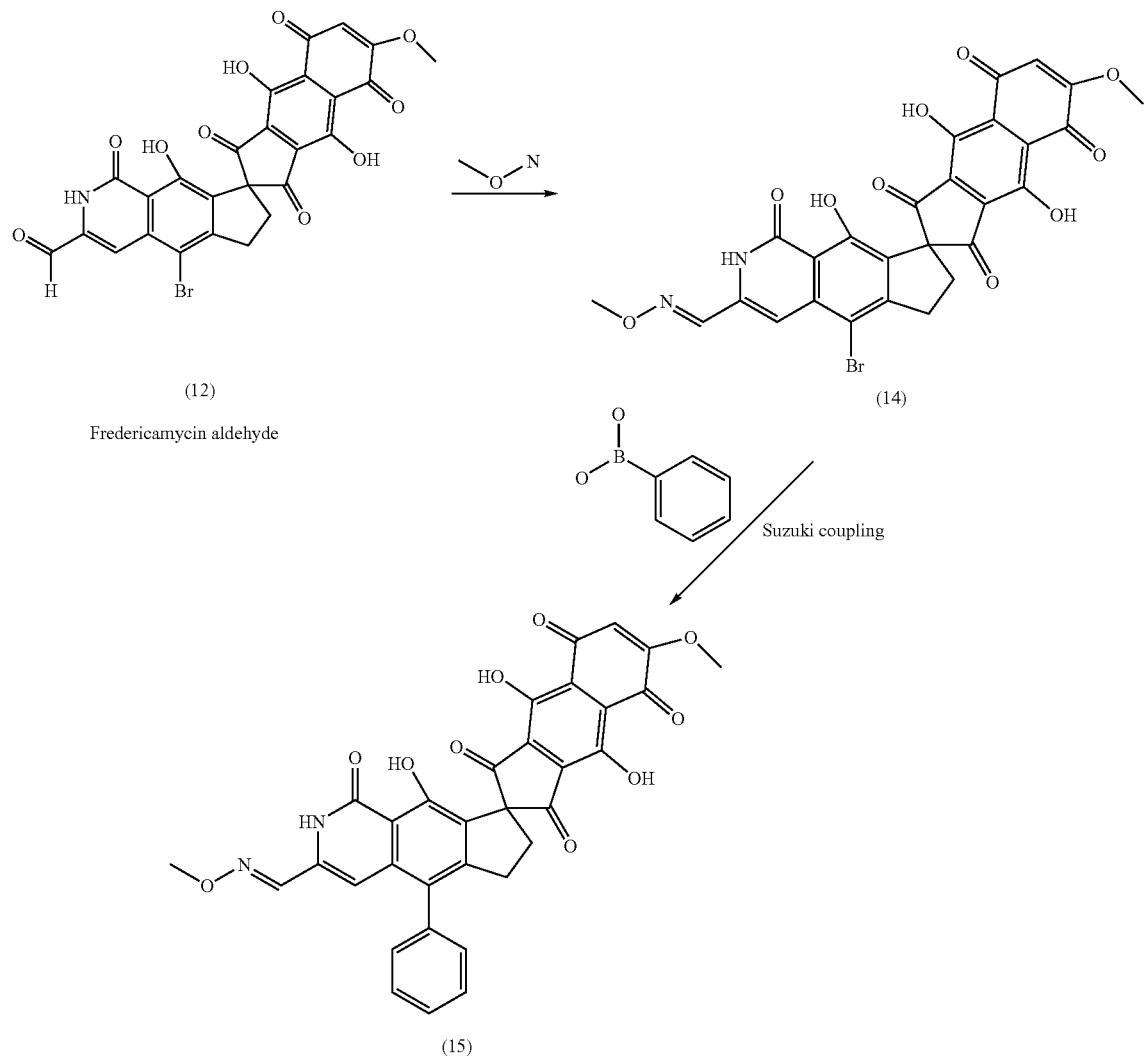

In the following diagrams, fredericamycin and its derivatives are used to show how analogous derivatives according to the invention can be prepared.

The compound (24) is the precursor of an N-methylated fredericamycin derivative (diagram 8).

Diagram 8

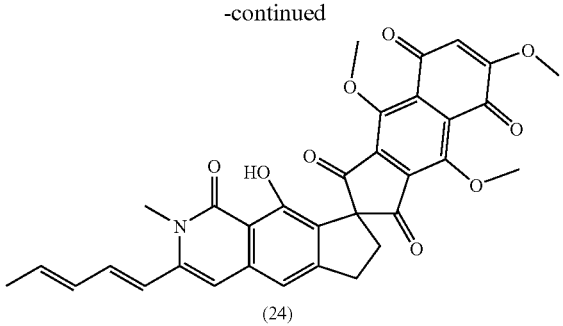

a) CH₃I, K₂CO₃, DMF, RT

Fredericamycin may be transformed by palladium/hydrogen almost quantatively to tetrahydro fredericamycin (25), and may be halogenated in the nucleus according to the above described methods, e.g. to the bromine compound (26) (see diagram 9):

Diagram 9

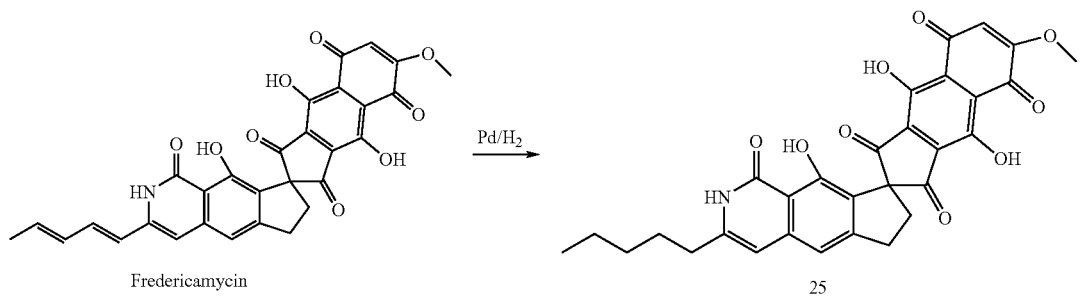

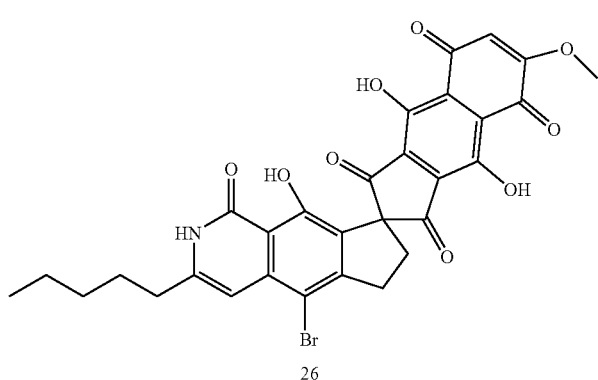

Surprisingly it has also been found that the methoxy groups in fredericamycin and the derivatives according to the invention can be exchanged under alkali or earth alkali acetate catalysis by oxygen nucleophiles such as alcohols or polyols. Thereby, the alcohols can carry a multitude of different substituents.

Diagram 10

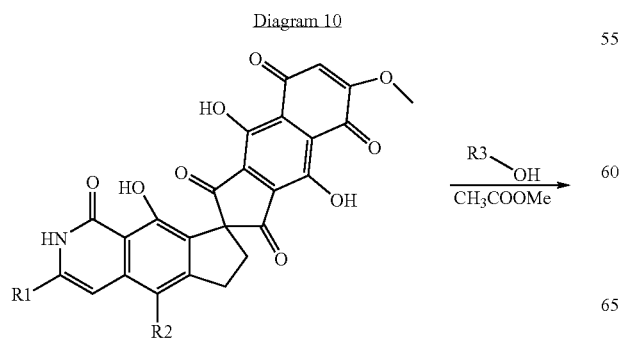

-continued

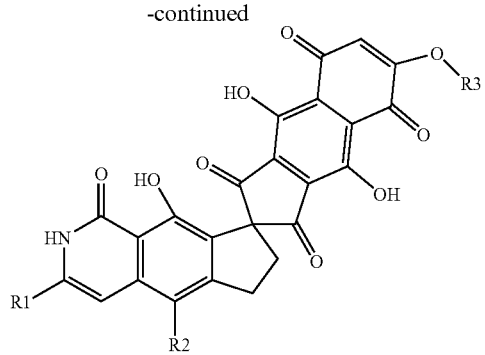

Exchange of the Methoxy Group at the F Ring

The exchange of the methoxy groups at the F ring of the fredericamycin and at the derivatives is possible by primary, secondary or aromatic amines. Thereby, the components are stirred with the appropriate primary or secondary amines at room temperature in DMF or in another inert solvent. With aromatic amines, a catalysis with Lewis acids such as stannous(IV)chloride, etc. is required.

Diagram 11

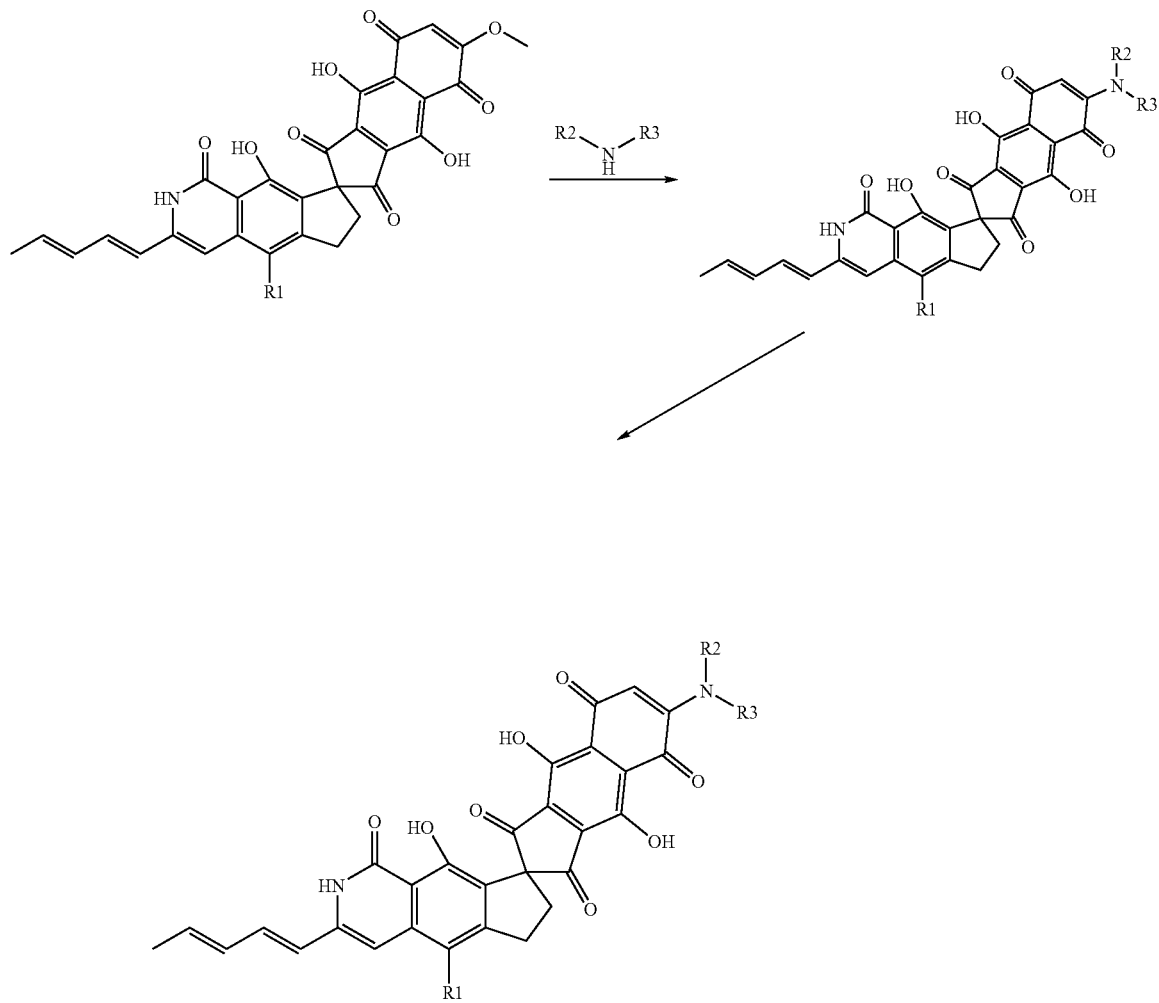

Preparation of Thioanalogoues of Fredericamycin Derivatives

By sulfurization of fredericamycin or its derivatives with Lawesson reagent or $P_4S_{10}$ in pyridine, the derivatives analogous to thiopyridone are accessible (see diagram 12).

Diagram 12

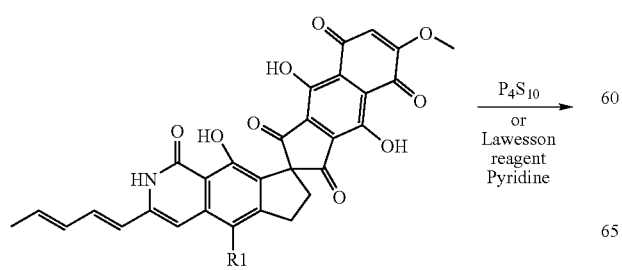

-continued

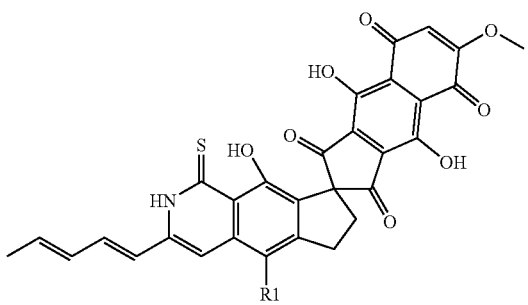

Fredericamycin (1) forms inclusion compounds such as (22) with polysugars such as α-cyclodextrin that have good water solubility compared to the original substance.

The dextrin inclusion compounds form easily if the components are mixed in the appropriate stoichiometric ratio in a suitable solvent such as DMSO.

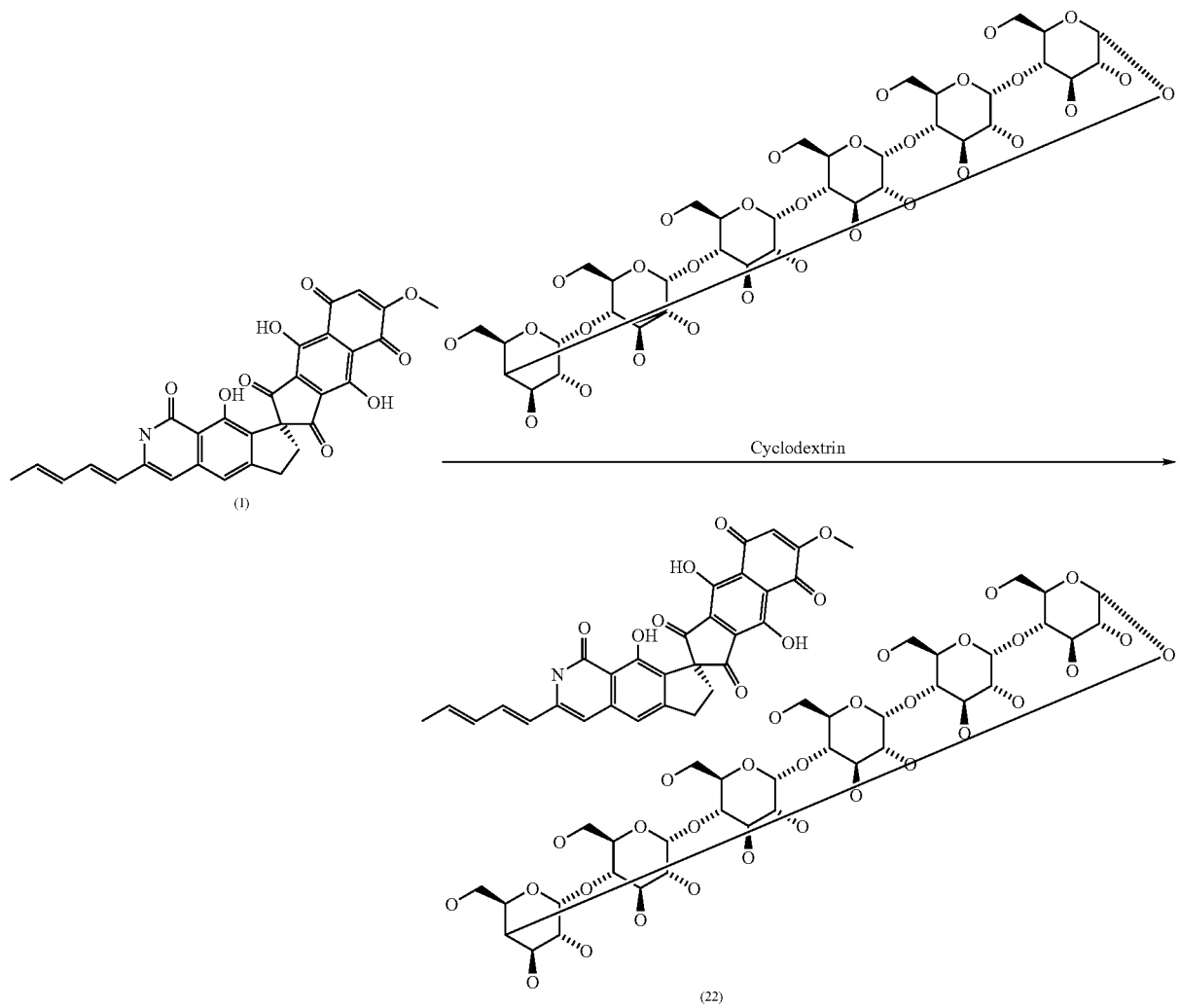

EXAMPLES

Example 1

1-Desoxy-5-C-[(8R)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-yl]pentitol (10)

Two hundred (200) mg (0.38 mmol) fredericamycin A (1) are dissolved in 30 mL dichloromethane. After addition of 20 mL methanol and 4.4 ml water, 350 mg (2.6 mmol) N-methylmorpholine-N-oxide are added. Under vigorous stirring, 0.2 ml of a 2.5% osinium(IV)oxide solution in t-butanol is added dropwise. The reaction mixture is acidified with 2-3 drops of trifluoracetic acid. After stirring for 48 hours, the reaction is complete according to HPLC control (RP18, acetonitrile water (0.2% acetic acid)). The reaction mixture is added to 400 ml water under vigorous stirring, and the dark red crystalline solid is sucked off through a filter. Drying in HV. Yield: 195 mg (87% of the theoretical value) dark red powder. ES$^-$: M/e=606.2 (M+−H), λmax: 504.0.

Example 2

(8S)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde (11)

1.) Fifty (50) mg (82.3 µmol) tetrahydroxy fredericamycin (tetrol (2)) are dissolved in 4 mL DMF. Under vigorous stirring, an aqueous sodium iodate solution (300 mg NaIO$_4$ in 1 mL water) is added dropwise within one hour. After 1 h stirring at room temperature, 2 drops of trifluoracetic acid are added. After stirring for another 30 min, the reaction solution is diluted with 3 ml DMF, and 150 mg NaIO$_4$ dissolved in 0.5 ml water are added.

After another hour, 100 mL water are added. The supernatant over the precipitate is sucked off, and dryed in HV. Dark red crystal powder. Yield: 41 mg (100% of the theoretical value). M/e=501.3, UV$_{max}$: 504.0 nm.

2.) One hundred and nine (109) mg (179 µmol) fredericamycin tetrol (2) are dissolved in 8 mL pyridine. 180 µL water are added. To the reaction mixture, 450 mg (1.08 mmol, 6 eq.) (polystryrylmethyl)trimethylammonium periodate resin are added. Then the mixture is stirred for 12 h at RT.

Example 3

(8S)-5-bromo-4',9,9'-trihydroxy-6'-methoxy-1,1',3',
5',8'-pentaoxo-1,1',2,3',5',6,7,8'-octahydrospiro[cy-
clopenta[g]isoquinoline-8,2'-cyclopenta[b]-naphtha-
lene]-1,1',3',5',8'(2H)-pentone (2)

Twenty (20) mg (37.1 µmol) fredericamycin (1) were dissolved in 250 µl DMF, and then 6.3 mg (35.3 µmol) N-bromosuccinimide in 250 µl DMF were added within one hour at 0° C. The reaction was stirred in a slowly thawing ice bath over night. Then, the DMF is removed in high vacuum, and the residue is purified by preparative HPLC.

Yield: 7 mg (32% of the theoretical value) red crystal mass. M/e=616.1/618.1; $\lambda_{max}$: 486.0 nm.

Example 4

(8S)-5-iodo-4',9,9'-trihydroxy-6'-methoxy-1,1',3',5',
8'-pentaoxo-1,1',2,3',5',6,7,8'-octahydrospiro[cyclo-
penta[g]isoquinoline-8,2'-cyclopenta[b]-naphtha-
lene]-1,1',3',5',8'(2H)-pentone (3)

Eighty four (84) mg (158 µmol) fredericamycin (1) were dissolved in 1.0 µl DMF, and then 33.0 mg (150.0 µmol) N-iodosuccinimide in 500 µl DMF were added within one hour at 0° C. The reaction was stirred in a slowly thawing ice bath over night. Then, the DMF is removed in high vacuum, and the residue (120 mg (14) with a content of 80%) is purified by preparative HPLC (gradient $CH_3CN$ 50-90% over 16 min.)

Yield: 18 mg (17% of the theoretical value) red crystal mass. M/e=665.0; $\lambda_{max}$: 484.0 nm.

Example 5

(8S)-4',9,9'-trihydroxy-5-bromo-6'-methoxy-1,1',3',
5',8'-pentaoxo-1,1',2,3',5',6,7,8'-octahydrospiro[cy-
clopenta[g]isoquinoline-8,2'-cyclopenta[b]-naphtha-
lene]-3-carbaldehyde (12)

Hundred (100) mg (200 µmol) fredericamycin aldehyde (4) are dissolved under argon in 5 ml DMF. Then, 200 µl of a 1M bromine solution in DMF is added. After stirring for 1.5 h at RT, another 20 µl bromine solution are added. According to HPLC monitoring, the reaction mixture is complete after 3.5 h.

Add to 150 ml water, and shake out with dichloromethane.
Yield: 96 mg (83% of the theoretical value) dark red powder. M/e=579/581; $\lambda_{max}$: 504.0.

Example 6

(8S)-4',9,9'-trihydroxy-5-iodo-6'-methoxy-1,1',3',5',
8'-pentaoxo-1,1',2,3',5',6,7,8'-octahydrospiro[cyclo-
penta[g]isoquinoline-8,2'-cyclopenta[b]-naphtha-
lene]-3-carbaldehyde (13)

Thirty (30) mg (49 µmol) fredericamycin tetrol (10) are dissolved in 1 ml dimethylsulfoxide/water 9/1. TO the reaction mixture 309 mg (2.4 mmol/g, 15 eq.) (polystyrylmethyl) trimethylammoniumperiodate resin are added. Then, the mixture is stirred for 48 h at RT. Then, it is filtered off the resin, diluted with water, and extracted 3× with dichloromethane to which 1% trifluoracetic acid has been added. After drying, it is concentrated until dry. Dark-red residue (HPLC clean). Yield 27.8 mg (90% of the theoretical value), M/e=626.2; $UV_{max}$: 500.0 nm

Example 7

(8S)-5-(trans-1-hexene-1yl)-4',9,9'-trihydroxy-6'-
methoxy-3-[(1E,3E)-penta-1,3-dienyl]-6,7-dihy-
drospiro[cyclopenta[g]isoquinoline-8,2'-cyclopenta
[b]-naphthalene]-1,1',3',5',8'(2H)-pentone (7)

Ten (10) mg (15 µmol) iodofredericamycin (3) are dissolved in 1 ml DMF under argon, then 4.8 mg (37.5 µmol) trans-1-hexene-1yl-boronic acid (4), 0.9 mg (0.78 µmol) tetrakis(triphenyl)palladium (0) and 75 µl (150 µmol) 2 M $Na_2CO_3$ solution are added. It is stirred for 1 h at room temperature, and is then heated to 90° C. for 12 h. The reaction mixture is divided between dichloromethane and 1 N hydrochloric acid. The product was purified by preparative HPLC (RP18, $CH_3CN$—$H_2O$).

Yield: 4.5 mg (48% of the theoretical value)

Example 8

(8S)-5-phenyl-4',9,9'-trihydroxy-6'-methoxy-3-[(1E,
3E)-penta-1,3-dienyl]-6,7-dihydrospiro[cyclopenta
[g]isoquinoline-8,2'-cyclopenta[b]-naphthalene]-1,1',
3',5',8'(2H)-pentone (8)

Ten (10) mg (15 µmol) iodofredericamycin (3) are dissolved in 1 ml DMF under argon, then 4.6 mg (37.7 µmol) phenylboronic acid (5), 0.9 mg (0.78 µmol) tetrakis(triphenyl)palladium (0) and 75 µl (150 µmol) 2 M $Na_2CO_3$ solution are added. It is stirred for 1 h at room temperature, and is then heated to 90° C. for 12 h. The reaction mixture is divided between dichloromethane and 1 N hydrochloric acid. The residue was purified by preparative HPLC (RP18, $CH_3CN$—$H_2O$).

Yield: 4.0 mg (43% of the theoretical value), M/e=615.0

Example 9

(8S)-5-(4-fluorophenyl)-4',9,9'-trihydroxy-6'-meth-
oxy-3-[(1E,3E)-penta-1,3-dienyl]-6,7-dihydrospiro
[cyclopenta[g]isoquinoline-8,2'-cyclopenta[b]-naph-
thalene]-1,1',3',5',8'(2H)-pentone (9)

Ten (10) mg (15 µmol) iodofredericamycin (3) are dissolved in 1 ml DMF under argon, then 5.3 mg (37.8 µmol) 4-fluorophenylboronic acid (6), 1.0 mg (0.87 µmol) tetrakis(triphenyl)palladium (0) and 35.2 mg (109 µmol) thallium carbonate are added. It is stirred for 12 h at 90° C. The reaction mixture is divided between dichloromethane and 1 N hydrochloric acid, and its residue was separated by preparative HPLC (RP18, $CH_3CN$—$H_2O$).

Yield: 2.5 mg (26% of the theoretical value), M/e=633.0

Example 10

The following compounds can be prepared analogously to the examples above:

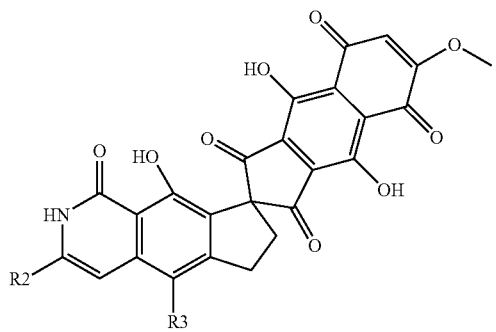

| Example 10 | Name | R2 | R3 |
|---|---|---|---|
| A | (8S)-5-(3-pyridyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 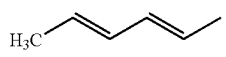 | 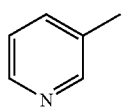 |
| B | (8S)-5-(4-pyridyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 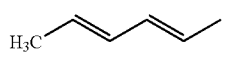 | 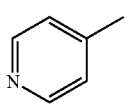 |
| C | (8S)-5-(5-indolyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 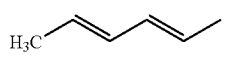 | 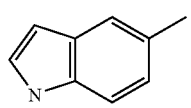 |
| D | (8S)-5-(4-dimethylaminophenyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3,5',8'(2H)-pentone | 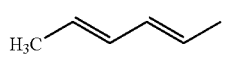 | 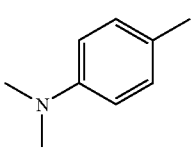 |
| E | (8S)-5-[4-(3,4-dimethylisoxazolyl)]-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 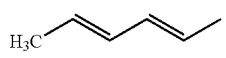 | 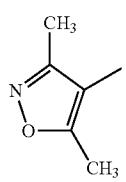 |
| F | (8S)-5-(3-furyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 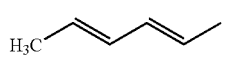 | 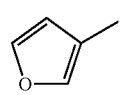 |
| G | (8S)-5-(4-benzyloxyphenyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 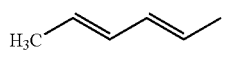 | 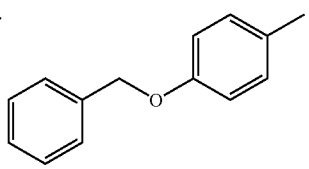 |
| H | (8S)-5-(4-methoxyphenyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 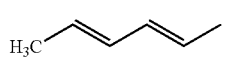 | 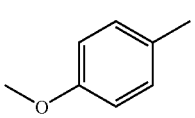 |

-continued

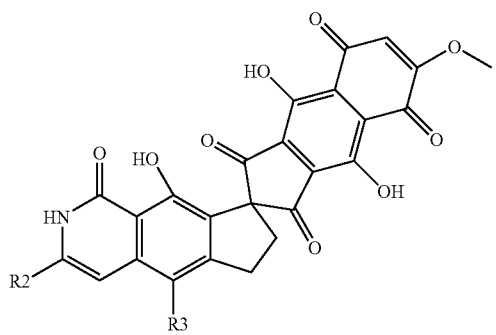

| Example 10 | Name | R2 | R3 |
|---|---|---|---|
| I | (8S)-5-(2-thiophenyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 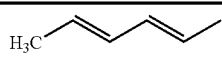 | 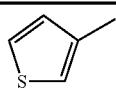 |
| J | (8S)-5-(3-thiophenyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 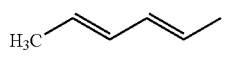 | 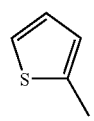 |
| K | (8S)-5-(4-carboxamidophenyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 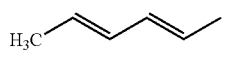 | 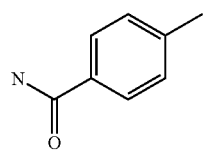 |
| L | (8S)-5-(1-dibenzofuranoyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 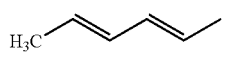 | 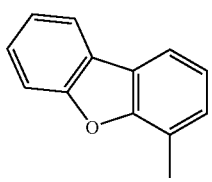 |
| M | (8S)-5-(2-N-methylpyrrolyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 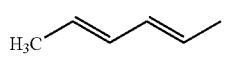 | 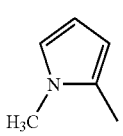 |
| N | (8S)-5-(2-pyridazinyl)-4',9,9'-trihydroxy-6'-methoxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone | 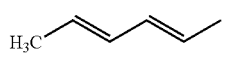 | 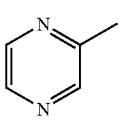 |
| O | (8S)-5-(phenyl)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-methyloxime | 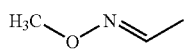 | 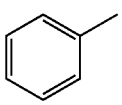 |
| P | (8S)-5-(2-thiophenyl)-4',9,9'-trihydroxy-6'-methoxy-1,1',3',5',8'-pentaoxo-1,1',2,3',5',6,7,8'-octahydrospiro[cyclopenta[g]isoquinoline-8,2'-cyclopenta[b]-naphthalene]-3-carbaldehyde O-methyloxime | 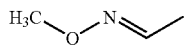 | 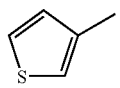 |

Example 11

Water Solubility of the Fredericamycin Derivatives

The water solubility of the various fredericamycin derivatives can be determined in 0.9% NaCl solution with a pH of 7.

The invention claimed is:

1. A compound according to the general formula Ia or Ib:

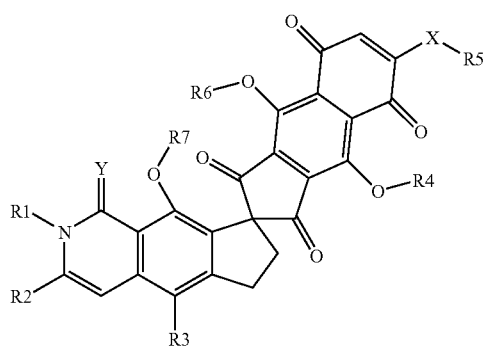

Ia

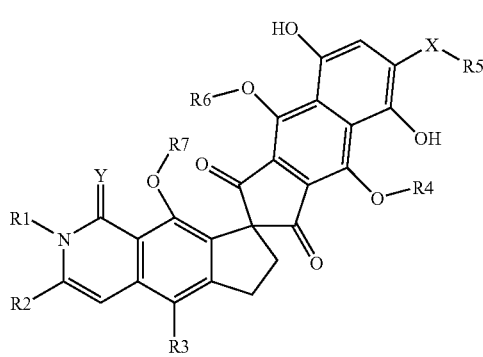

Ib wherein in each,

R1 is H, $C_1$-$C_6$ alkyl, cycloalkyl, or $C_1$-$C_4$ alkylcycloalkyl;

R2 is $C_1$-$C_{14}$ alkyl, $C_2$-$C_{14}$ alkenyl, 1,3-butadienyl, 1-butane, $C_1$-$C_4$ alkylaryl, heteroaryl, $C_1$-$C_4$ alkylheteroaryl, cycloalkyl, $C_1$-$C_4$ alkyl-cycloalkyl, heterocycloalkyl, $C_1$-$C_4$ alkylheterocycloalkyl, $C_mH_{2m+o-p}Y''_p$, CH$_2$NHCOR21, CH$_2$NHCSR21, CH$_2$S(O)nR21, with n=0, 1, 2, CH$_2$SCOR21, CH$_2$OSO$_2$—R21, CHO, CH═NOH, CH(OH)R21, —CH═NOR21, —CH═NOCOR21, —CH═NOCH$_2$CONR21R22, —CH═NOCH(CH$_3$)CONR21R22, —CH═NOC(CH$_3$)$_2$CONR21R22, —CH═N—NHCO—R23, —CH═N—NHCO—CH$_2$NHCOR21, —CH═N—O—CH$_2$NHCOR21, —CH═N—NHCS—R23, —CH═CR24R25 (trans or cis), COOH, COOR21, CONR21R22, —CH═NR21, —CH═N—NR21R22,

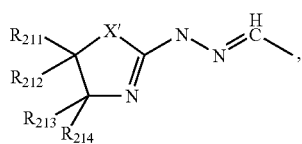

—CH═N—NHSO$_2$ aryl, or —CH═N—NHSO$_2$ heteroaryl,
wherein m is 1 to 6, o is 1, p is 1 to 2m+o;
m is 2 to 6, o is -1, p is 1 to 2m+o; or
m is 4 to 6, o is -2, p is 1 to 2m+o;

Y'' is independently from each other selected from the group consisting of halogen, OH, OR21, NH$_2$, NHR21, NR21R22, SH and SR21; and wherein X' is NR215, O, or S; and R211, R212, R213, R214, R215 are independently from each other H or $C_1$-$C_6$ alkyl;

R21, R22 are independently from each other $C_1$-$C_{14}$ alkyl, $C_1$-$C_{14}$ alkanoyl, $C_1$-$C_6$ alkylhydroxy, $C_1$-$C_6$ alkylamino, $C_1$-$C_6$alkylamino-$C_1$-$C_6$ alkyl, $C_1$-$C_6$ alkylamino-di-$C_1$-$C_6$ alkyl, cycloalkyl, $C_1$-$C_4$ alkylcycloalkyl, heterocycloalkyl, $C_1$-$C_4$ alkylheterocycloalkyl, aryl, aryloyl, $C_1$-$C_4$ alkylaryl, heteroaryl, heteroaryloyl, $C_1$-$C_4$ alkylheteroaryl, cycloalkanoyl, $C_1$-$C_4$ alkanoylcycloalkyl, heterocycloalkanoyl, $C_1$-$C_4$ alkanoylheterocycloalkyl, $C_1$-$C_4$ alkanoylaryl, $C_1$-$C_4$ alkanoylheteroaryl, or mono- and di-sugars linked through a C atom which would carry an OH group in the sugar, wherein the sugars are independently from each other selected from the group consisting of glucuronic acid and its stereo isomers at all optical atoms, aldopentoses, and aldohexoses, including their desoxy compounds;

R23 independently of R21, is R21, a CH$_2$-pyridinium salt, or a CH$_2$-tri-$C_1$-$C_6$ alkylammonium salt;

R24 independently of R21, is R21, H, CN, COCH$_3$, COOH, COOR21, CONR21R22, NH$_2$, or NHCOR21;

R25 independently of R21, is R21, H, CN, COCH$_3$, COOH, COOR21, CONR21R22, NH$_2$, or NHCOR21; or R24, R25 together are $C_4$-$C_8$ cycloalkyl;

R3 is $C_2$-$C_{14}$ alkyl, $C_2$-$C_{14}$ alkenyl, $C_2$-$C_{14}$ alkinyl, aryl, $C_1$-$C_4$ alkylaryl, heteroaryl, $C_1$-$C_4$ alkylheteroaryl, wherein the aryls or heteroaryls may be substituted with another aryl, $C_1$-$C_4$ alkylaryl, O-aryl, $C_1$-$C_4$ alkyl-O-aryl, heteroaryl, $C_1$-$C_4$ alkylheteroaryl, O-heteroaryl or $C_1$-$C_4$ alkyl-O-heteroaryl, cycloalkyl, $C_1$-$C_4$ alkylcycloalkyl, heterocycloalkyl, $C_1$-$C_4$ alkylheterocycloalkyl, $C_mH_{2m+o-p}Y'_p$, CH$_2$NHCOR31, CH$_2$NHCSR31, CH$_2$S(O)nR31, CH$_2$SCOR31, CH$_2$OSO$_2$—R31, CHO, CH═NOH, CH(OH)R31, —CH═NOR31, —CH═NOCOR31, —CH═NOCH$_2$CONR31R32, —CH═NOCH(CH$_3$)CONR31R32, —CH═NOC(CH$_3$)$_2$CONR31R32, —CH═N—NHCO—R33, —CH═N—NHCO—CH$_2$NHCOR31, —CH═N—O—CH$_2$NHCOR31, —CH═N—NHCS—R33, —CH═CR34R35 (trans or cis), COOH, COOR31, CONR31R32, —CH═NR31, —CH═N—NR31R32,

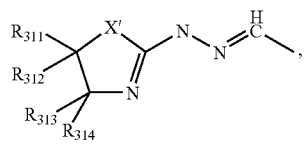

(with X'═NR315, O, S, and R311, R312, R313, R314, R315 being independently from each other H or $C_1$-$C_6$ alkyl),
—CH═N—NHSO$_2$ aryl, or —CH═N—NHSO$_2$-heteroaryl,
wherein m is 2-6, o is 1 or -1, and p is 1 to 2m+o; or
m is 4-6, o is -3 and p is 1 to 2m+o; and Y' is independently from each other selected from the group consisting of halogen, OH, OR31, NH2, NHR31, NR31R32, SH, and SR31; and wherein n is 0, 1 or 2;

R31, R32 mean independently from each other $C_1$-$C_{14}$ alkyl, $C_1$-$C_{14}$ alkanoyl, $C_1$-$C_6$ alkylhydroxy, $C_1$-$C_6$ alkylamino, $C_1$-$C_6$ alkylamino-$C_1$-$C_6$ alkyl, $C_1$-$C_6$ alkylamino-di-$C_1$-$C_6$ alkyl, cycloalkyl, $C_1$-$C_4$ alkylcycloalkyl, heterocycloalkyl, $C_1$-$C_4$ alkylheterocycloalkyl, aryl, aryloyl, $C_1$-$C_4$ alkylaryl, heteroaryl, heteroaryloyl, $C_1$-$C_4$ alkylheteroaryl, cycloalkanoyl, $C_1$-$C_4$ alkanoylcycloalkyl, heterocycloalkanoyl, $C_1$-$C_4$ alkanoylheterocycloalkyl, $C_1$-$C_4$ alkanoylaryl, $C_1$-$C_4$ alkanoylheteroaryl, alkanoylaryl, $C_1$-$C_4$ alkanoylheteroaryl, or mono- and di-sugars linked through a C atom which would carry an OH group in the sugar, wherein the sugars are independently from each other selected from the group consisting of glucuronic acid and its stereo isomers at all optical atoms, aldopentoses, and aldohexoses, including their desoxy compounds;

R33 independently of R31, is R31, a $CH_2$-pyridinium salt, or a $CH_2$-tri-$C_1$-$C_6$ alkylammonium salt;

R34 independently of R21, is R31, H, CN, $COCH_3$, COOH, COOR21, CONR31R32, $NH_2$, or NHCOR31; or R35 independently of R31, is R31, H, CN, $COCH_3$, COOH, COOR31, CONR31R32, $NH_2$, or NHCOR31;

R34, R35 together are $C_4$-$C_8$ cycloalkyl;

R5 is H, $C_1$-$C_6$ alkyl, cycloalkyl, $C_1$-$C_4$ alkylcycloalkyl, heterocycloalkyl, $C_1$-$C_4$ alkylheterocycloalkyl, aryl, $C_1$-$C_4$ alkylaryl, heteroaryl, or $C_1$-$C_4$ alkylheteroaryl;

R4, R6, R7 independently from each other are H, $C_1$-$C_6$ alkyl, or CO—R41;

R41 independently of R21, is R21;

X is O, S, NH, or N—R8, wherein R8 independently from R5 is R5, or R5 and R8, together with the N, form a ring with 4, 5, 6, 7, or 8 members, which may optionally contain still another heteroatom selected from the group consisting of N, O, and S;

or X—R5 may together be H;

Y is O, S, or NR9, wherein R9 is H or $C_1$-$C_6$ alkyl;

or a stereoisomer, tautomer or physically tolerable salt thereof.

2. The compounds according to claim 1, wherein Formula Ia or Ib adopt the stereochemistry of Formula IIa or IIb

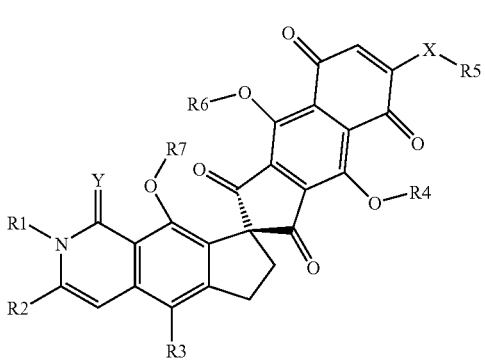

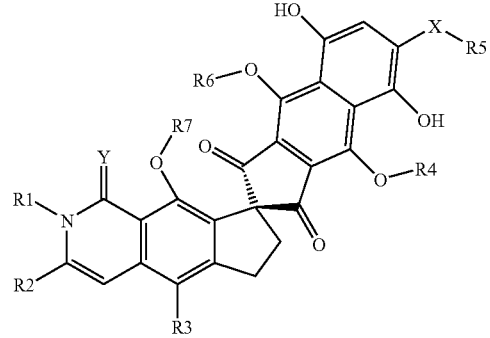

3. The compound according to claim 1, wherein

R1 is H, $C_1$-$C_5$ alkyl, or cycloalkyl;

R2 is $C_1$-$C_5$ alkyl, $C_1$-$C_4$ alkylaryl, $C_2$-$C_5$ alkenyl, heteroaryl, $C_1$-$C_4$ alkylheteroaryl, $CHF_2$, $CF_3$, polyol side chain, CHOH—CHOH—CHOH—CHOH—$CH_3$, CHOH—CHOH—CH=CH—$CH_3$, CH=CH—CHOH—CHOH—$CH_3$, $CH_2$Y'''(Y'''=F, Cl, Br, I), $CH_2NH_2$, $CH_2$NR21R22, $CH_2$NHCOR23, $CH_2$NHCSR23, $CH_2$SH, $CH_2$S(O)nR21, with n=0, 1, 2, $CH_2$SCOR21, $CH_2$OH, $CH_2$OR21, $CH_2OSO_2$—R21, CHO, $CH(OR21)_2$, $CH(SR21)_2$, CN, CH=NOH, CH=NOR21, CH=NOCOR21, CH=N—NHCO—R23, CH=CR24, R25 (trans or cis), COOH, COOR21, CONR21R22, —CH=NR21, —CH=N—NR21R22,

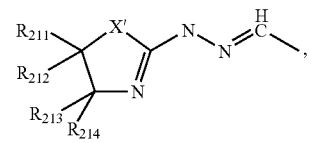

—CH=N—$NHSO_2$-aryl, —CH=N—$NHSO_2$-heteroaryl, or wherein X' is NR215, O, or S; and R211, R212, R213, R214, and R215 are independently from each other are H or $C_1$-$C_6$ alkyl;

R21, R22 independently from each other are $C_1$-$C_6$ alkyl, cycloalkyl, aryl, $C_1$-$C_4$ alkylaryl, heteroaryl, or $C_1$-$C_4$ alkylheteroaryl;

R23, independently of R21, is R21, a $CH_2$-pyridinium salt, or a $CH_2$-tri-$C_1$-$C_6$ alkylammonium salt;

R24 independently of R21, is R21, H, CN, $COCH_3$, COOH, COOR21, CONR21R22, $NH_2$, or NHCOR21;

R25 independently of R21, is R21, H, CN, $COCH_3$, COOH, COOR21, CONR21R22, $NH_2$, or NHCOR21; or R24, R25 together are $C_4$-$C_8$ cycloalkyl;

R3 is $C_2$-$C_{14}$ alkyl, $C_2$-$C_{14}$ alkenyl, $C_2$-$C_{14}$ alkinyl, aryl, $C_1$-$C_4$ alkylaryl, heteroaryl or $C_1$-$C_4$ alkylheteroaryl, wherein the aryls or heteroaryls may be substituted with another aryl, $C_1$-$C_4$ alkylaryl, O-aryl, $C_1$-$C_4$ alkyl-O-aryl, heteroaryl, $C_1$-$C_4$ alkylheteroaryl, O-heteroaryl or $C_1$-$C_4$ alkyl-O-heteroaryl;

R5 is H, $C_1$-$C_3$ alkyl, or cycloalkyl;

R4, R6, R7 independently from each other are H, $C_1$-$C_5$ alkyl, or CO—R41;

R41 independently of R21, is R21;

X is O, S, NH, or N—R8;

Y is O, S, or NH.

4. The compound according to claim 1 in the form of an inclusion compound with cyclodextrin.

5. The compound according to claim 2 wherein

R1 is H, $C_1$-$C_5$ alkyl, or cycloalkyl;

R2 is $C_1$-$C_5$ alkyl, $C_1$-$C_4$ alkylaryl, $C_2$-$C_5$ alkenyl, heteroaryl, $C_1$-$C_4$ alkylheteroaryl, $CHF_2$, $CF_3$, polyol side chain, CHOH—CHOH—CHOH—CHOH—$CH_3$, CHOH—CHOH—CH=CH—$CH_3$, CH=CH—CHOH—CHOH—$CH_3$, $CH_2Y$ (Y'''=F, Cl, Br, I), $CH_2NH_2$, $CH_2NR21R22$, $CH_2NHCOR23$, $CH_2NHCSR23$, $CH_2SH$, $CH_2S(O)nR21$, with n=0, 1, 2, $CH_2SCOR21$, $CH_2OH$, $CH_2OR21$, $CH_2OSO_2$-R21, CHO, $CH(OR21)_2$, $CH(SR21)_2$, CN, CH=NOH, CH=NOR21, CH=NOCOR21, CH=N—NHCO—R23, CH=CR24, R25 (trans or cis), COOH,

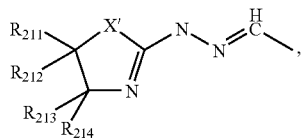

COOR21, CONR21R22, —CH=NR21, —CH=N—NR21R22,

—CH=N—$NHSO_2$-aryl, —CH=N—$NHSO_2$-heteroaryl, or CH=N—NHC—R23, wherein X' is NR215, O, or S; and R211, R212, R213, R214, and R215 are independently from each other are H or $C_1$-$C_6$ alkyl;

R21, R22 independently from each other are $C_1$-$C_6$ alkyl, cycloalkyl, aryl, $C_1$-$C_4$ alkylaryl, heteroaryl, or $C_1$-$C_4$ alkylheteroaryl;

R23 independently of R21, is R21, a $CH_2$-pyridinium salt, or a $CH_2$-tri-$C_1$-$C_6$ alkylammonium salt;

R24 independently of R21, is R21, H, CN, $COCH_3$, COOH, COOR21, CONR21R22, $NH_2$, or NHCOR21;

R25 independently of R21, is R21, H, CN, $COCH_3$, COOH, COOR21, CONR21R22, $NH_2$, or NHCOR21; or R24, R25 together are $C_4$-$C_8$ cycloalkyl;

R3 is $C_2$-$C_{14}$ alkyl, $C_2$-$C_{14}$ alkenyl, $C_2$-$C_{14}$ alkinyl, aryl, $C_1$-$C_4$ alkylaryl, heteroaryl, or $C_1$-$C_4$ alkylheteroaryl, wherein the aryls or heteroaryls may be substituted with another aryl, $C_1$-$C_4$ alkylaryl, O-aryl, $C_1$-$C_4$ alkyl-O-aryl, heteroaryl, $C_1$-$C_4$ alkylheteroaryl, O-heteroaryl or $C_1$-$C_4$ alkyl-O-heteroaryl;

R5 is H, $C_1$-$C_3$ alkyl, or cycloalkyl;

R4, R6, R7 independently from each other are H, $C_1$-$C_5$ alkyl, or CO—R41;

R41 independently of R21, is R21;

X is O, S, NH, or N—R8;

Y is O, S, or NH.

6. A pharmaceutical composition comprising a compound of claim 1 and a pharmaceutically acceptable carrier or adjuvant.

7. A pharmaceutical composition comprising a compound of claim 2 and a pharmaceutically acceptable carrier or adjuvant.

* * * * *